United States Patent [19]

Logue

[11] Patent Number: 5,939,880

[45] Date of Patent: Aug. 17, 1999

[54] POLAR COORDINATE SENSOR DRIVEN BY A POLY-PHASE STATOR CORE

[76] Inventor: Delmar Leon Logue, R.R. #1, Box 60, Herrick, Ill. 62431

[21] Appl. No.: 09/023,516

[22] Filed: Feb. 13, 1998

Related U.S. Application Data

[63] Continuation-in-part of application No. 08/599,775, Feb. 12, 1996, Pat. No. 5,793,204, application No. 08/685,854, Jul. 24, 1996, Pat. No. 5,754,043, and application No. 08/832,100, Apr. 3, 1997.

[51] Int. Cl.$^6$ .......................... G01N 27/72; G01N 27/90; G01R 33/00; G01B 7/00
[52] U.S. Cl. .................... 324/232; 324/207.26; 324/239; 324/240; 324/242
[58] Field of Search .......................... 324/207.17–207.19, 324/207.26, 226–233, 239–243

[56] References Cited

U.S. PATENT DOCUMENTS

| 4,495,466 | 1/1985 | Lakin | 324/242 |
|---|---|---|---|
| 4,503,714 | 3/1985 | Winterhoff | 324/209 X |
| 4,818,935 | 4/1989 | Takahashi et al. | 324/232 |
| 5,399,968 | 3/1995 | Sheppard et al. | 324/232 X |
| 5,754,043 | 5/1998 | Logue | 324/240 X |

FOREIGN PATENT DOCUMENTS

| 1368767 | 1/1988 | U.S.S.R. | 324/232 |
|---|---|---|---|

*Primary Examiner*—Gerard Strecker

[57] ABSTRACT

Poly-phase induction motor-stator rotating magnetic fields are utilized as driving cores coupled to polar coordinate sensors for higher driving flux utilization and size reduction. External internal and combinational driving core structures are disclosed. An unsegmented stator having an extended longitudinal coupling portion is also disclosed.

5 Claims, 4 Drawing Sheets

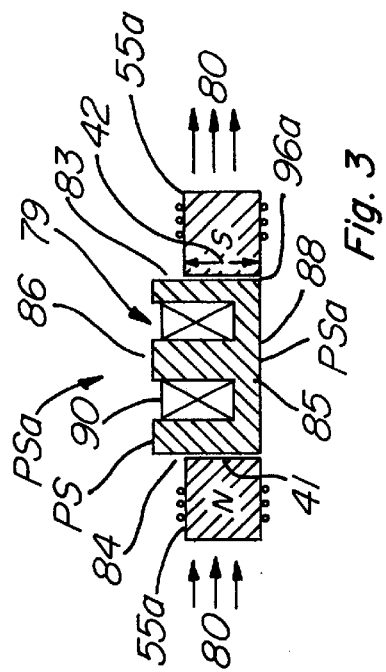
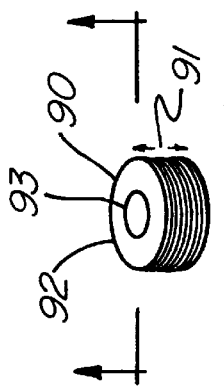
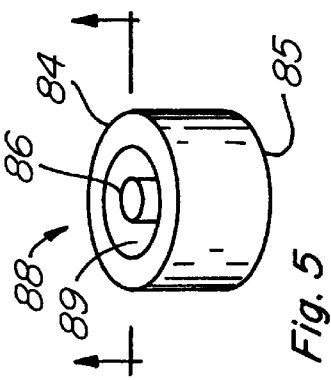
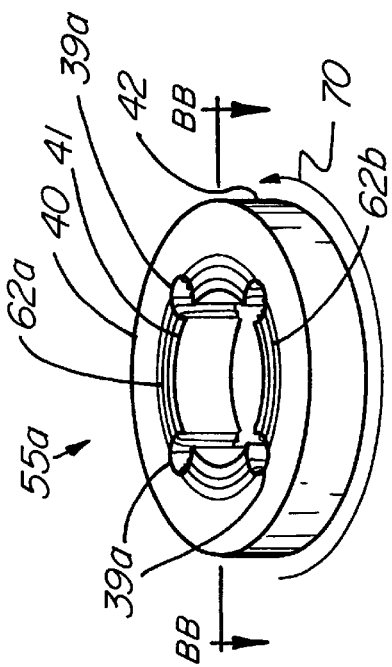
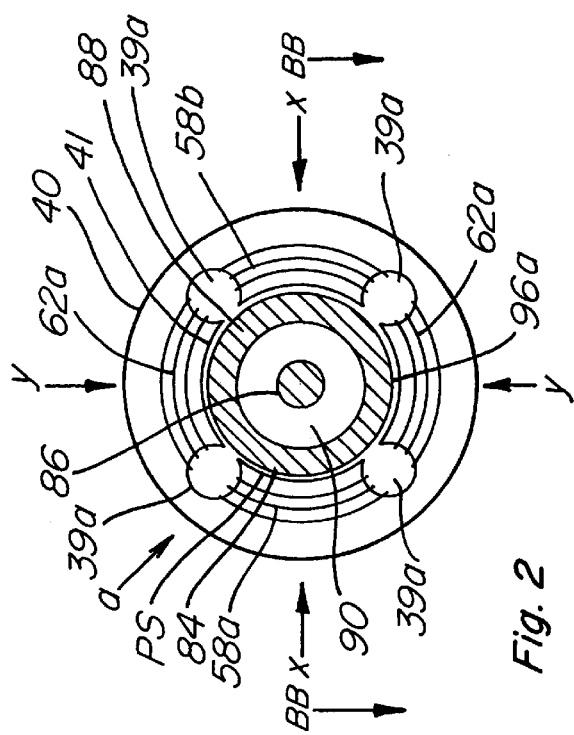

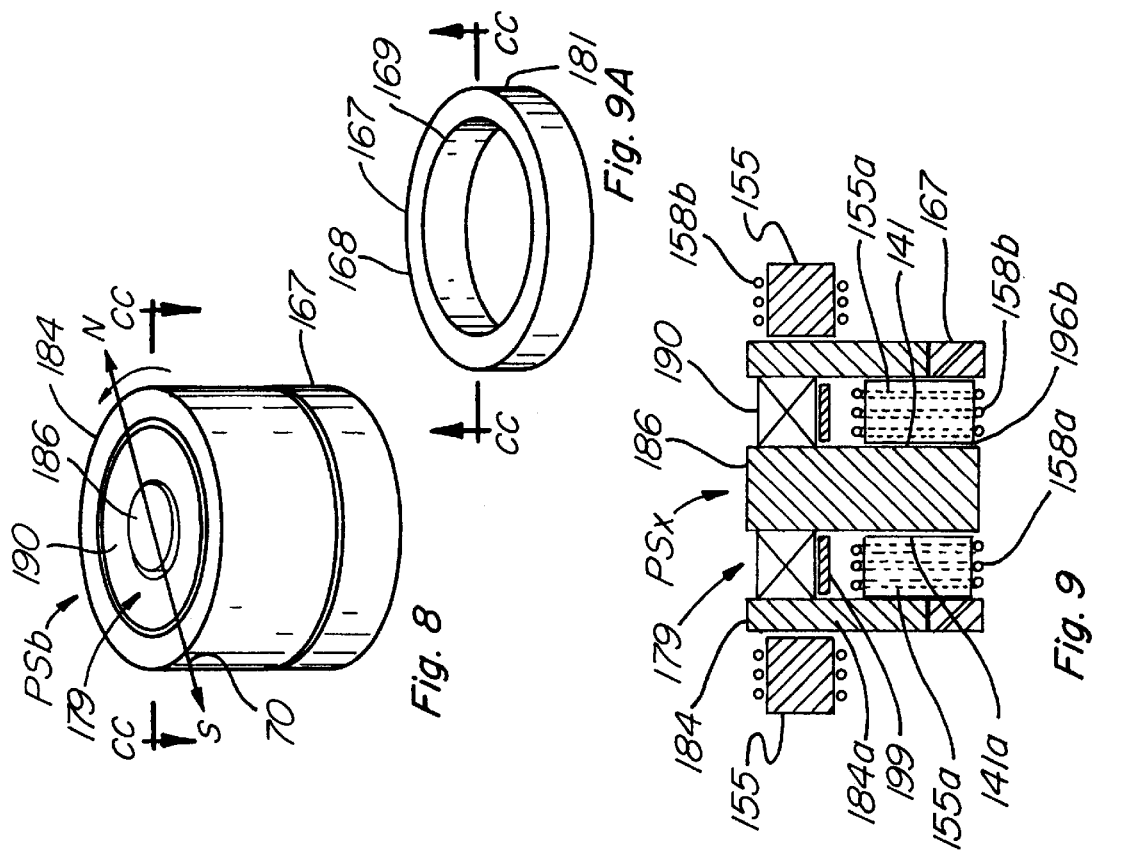

5,939,880

POLAR COORDINATE SENSOR DRIVEN BY A POLY-PHASE STATOR CORE

RELATED PATENT APPLICATIONS

This Patent Application is a continuation-in-part of the following patent applications:

Ser. No. 08/599,775 filed Feb. 12, 1996, now U.S. Pat. No. 5,793,204.

Ser. No. 08/685,854 filed Jul. 24, 1996, now U.S. Pat. No. 5,754,043.

Ser. No. 08/832,100 filed Apr. 03, 1997 pending.

The present poly-phase motor stator driving core was originally filed in Disclosure Document No. 402480 dated Jul. 12, 1996.

This invention relates to the previously disclosed inventions e.g. angular resolvers, proximity sensors, eddy current probes, hexagonal sensing array and polar coordinate joystick, bearing the generic term polar coordinates sensor (U.S. Pat. Nos. 5,404,101; 5,532,591; 5,548,212; 5,554,933; 5,559,432 and 5,574,367).

The basic polar coordinate sensor comprises a driving core wound with poly-phase (previously referred to as sine-cosine) excitation coils and a pick-up core having one or more pick-up coils wound around a central pole or a hexagonal array of poles.

The present invention utilizes rotating field stator structure concepts originating with Tesla, e.g. all poly-phase induction motor stator designs. All present and future developed magnetic core materials are suitable and deemed covered, presently ferrite is the preferred magnetic material.

The primary objectives of the invention are to increase sensing pattern flux density, simplify construction, and size reduction. The Logue patent application Ser. Nos. 07/842,244, 08/142,933, 08/187,072, 08/217,738, 08/267,511, 08/388,825, 08/685,854 and 08/599,775 utilized several variations-of hollow toroid driving cores. The Logue patent application Ser. No. 08/685,854 disclosed cross arm driving core ideas. The motor stator types disclosed have a higher net flux utilization than the earlier hollow toroid driving core embodiments.

BRIEF DESCRIPTION OF THE DRAWINGS

FIG. 1 is a perspective view of an external field stator driving core for driving a polar coordinates sensor.

FIG. 2 is a radial view of the driving core of FIG. 1 with a mounted polar sensor.

FIG. 3 is a cross-sectional view of the stator type driving core of FIG. 2 also showing the mounted polar sensor cross-section.

FIG. 4 is a perspective view of a polar sensor pick-up coil to illustrate three dimensional flux coupling factors.

FIG. 5 is a perspective view of an elementary polar sensor pick-up core.

FIG. 5A is a resonant tank circuit which includes the pick-up coil.

FIG. 6 is a perspective view of an internal field driving core for driving a cylindrical shaped pole element.

FIG. 7 is a radial view of the internal field driving core of FIG. 6.

FIG. 8 is a perspective view of probe PSb utilizing an internal field driving core driving a cylindrical pole encircling a central pole wound with a pick-up coil.

FIG. 9 is a cross-sectional view of internally driven probe PSx.

FIG. 9A is a perspective view of a high reluctance shield in the form of a nonferrous ring around the rear end of the driving core of FIG. 6, for reflecting the driving flux toward the sensing end of the probe.

BASIC PRINCIPLES

Figure 10:
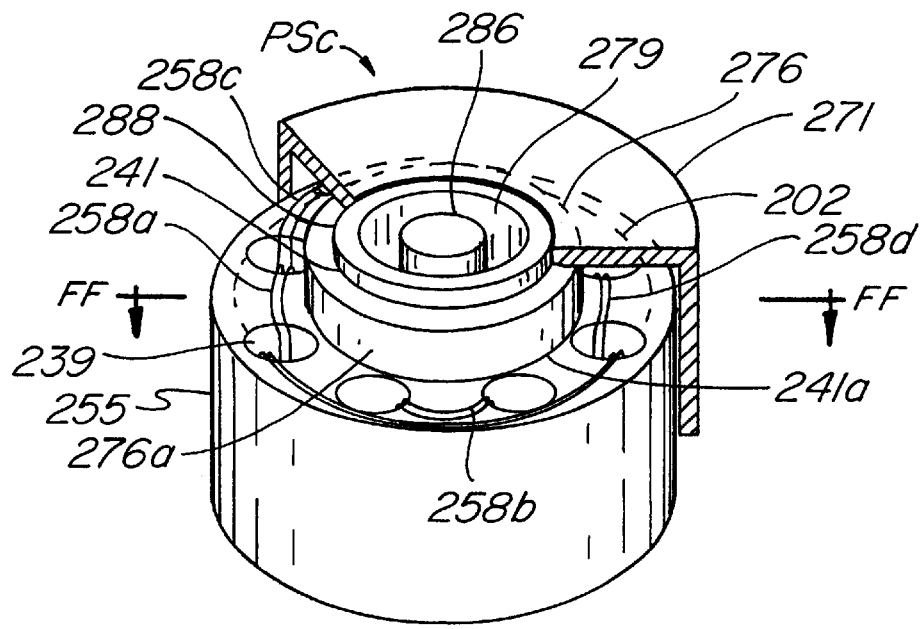
FIG. 10 is an isometric view (casing cut away 220 degrees) of eddy current probe PSc, utilizing an external stator having an integral longitudinal flange for a greater area flux coupling to the pick-up core.

Research to date indicates a synergism of basic electromagnetic principles embodied in the following key words.

Key I) Parametric Coupling/Coplanar Driven pick-up coil.

The driving flux natural direction is orthogonal to the pick-up core axis i.e. the pick-up coil turns are disposed in the plane of the driving flux therefore inherently nulled.

Key II) A Coupling Coefficient (longitudinal/tangential).

This flux gap allows the pick-up core inductance to ring as a true reflection of a flaw imbalance.

Key III) An Oscillatory Tank Circuit.

Key IV) Swept Angular Velocity (SAV), formerly called Variable Angular Velocity (VAV).

Key V) A Precessing Elliptical sensing pattern.

These key words will be further defined as dispersed throughout the detailed description of the invention.

DESCRIPTION OF THE PREFERRED EMBODIMENTS

The External Field Stator Driving Core

FIGS. 1–5 are illustrative of an eddy current (not limited to eddy current effects) probe utilizing a driving stator of this invention (an external field). The generic polar coordinates sensor (FIGS. 4 and 5) comprises a pick-up core 88 formed of a high permeability material, such as ferrite (a slotless pot core half) and a pick-up coil 90 having many turns. Pick-up core 88, also has a cylindrical outer pole 84, a cylindrical central pole 86 and a base portion 85. Pick-up coil 90 has an inner diameter 93, an outer diameter 92, and a longitudinal length 91. Pick-up coil 90 is disposed concentrically within toroidal space 89. Driving core 55a is formed of a high permeability material, such as laminated steel or ferrite, depending on the excitation frequency range. FIG. 1 is a perspective view of driving core 55a similar to a two phase induction motor stator with orthogonal field coils 58a, 58b (x-axis) 62a, 62b (y-axis) wound through slots 39a. Driving core 55a may be divided into any number of pole segments, odd or even, and all sinusoidal winding methods may be utilized. Semi-circle 70 represents the rotating driving field (example direction). As induction motor stators utilize external and internal stator fields, the disclosed eddy current probes make use of both external, internal, and a combinational arrangement. Driving stator 55a has an outside diameter 40, an inside driving diameter (bore 41) and an axial length 42. FIG. 2 is a radial view of driving core 55a showing a polar sensor PS (pick-up assembly proper) mounted concentric in bore 41 (rotor location if this were a motor).

FIG. 3 is a cross-section longitudinal view taken along lines BB showing polar sensor PS mounted partially within bore 41 leaving an extending portion 83 to form an annular sensing face 79. The driving flux lines 80 couple orthogonally to the axis of pick-up core 88, thus the winding turns of pick-up coil 90 are said to be coplanar driven (key I). Also, there is an annular coupling gap (key II) in the driving flux circuit of pick-up core 88 within bore 41 i.e. there being a small difference in the bore I.D. and the pick-up core O.D. to form a concentric magnetic gap 96a in the driving flux path. A primary signal nulling requirement is the concentricity of the pick-up core axis within bore 41. Constancy of annular gap 96a width is one of the chief factors affecting the tuning of a perfect null. The experimential gap width being <0.001", rigidity being the prime requisite. The pick-up coil turns must also be concentric to the annular space 89. The external field driving core embodiments (PSa, PSc) of this disclosure also have special application as driving cores for the angular resolver and proximity sensor of the Logue U.S. Pat. No. 5,404,101 and including the joystick invention disclosed in the Logue U.S. Pat. No. 5,559,432 providing an overall size reduction. Further by longitudinal lengthening of the stator two pick-up cores may be driven (base portions disposed adjacently) as in the the cross arm version disclosed in patent application Ser. No. 08/685,854.

The theory of operation is as follows, however, it is not intended that the invention in any way be restricted by this explanation. Analysis indicates, flux linkage through pick-up coil 90 is the result of a type of parametric coupling found in equation: E=Ri+L(di/dt)+i(dL/dt), the parametric term being i (dL/dt). In the preferred embodiments of the invention pick-up coil 90 (190, 290a) is shunted by a capacitor 75 in FIG. 5A, forming a series resonant-tank circuit 74. Tank circuit oscillatory action in magnetically balanced coils and cores is known in prior art, e.g. Wiegand U.S. Pat. No. 2,910,654, col. 3 lines 5–75, the Paraformer (Wanlass Electric Co. patent assignee).

Figure 14:
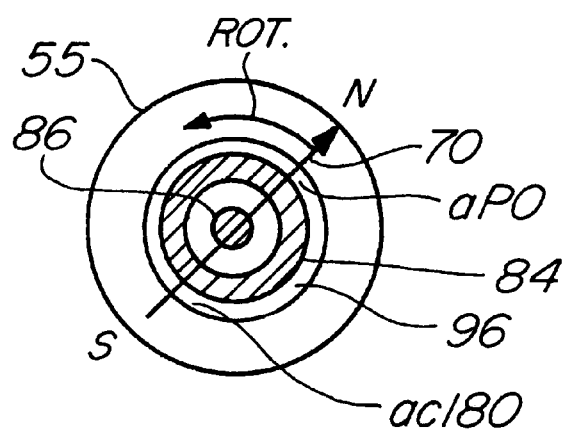
FIG. 14, is a diagrammatic sensing face view of the subject probe illustrating pick-up core flux coupling parameters.

To continue this anslysis, refer now to FIG. 14, being an axial view of pick-up core 88 and driving core 55 (excitation windings and slots are not shown for clarity). Cylindrical outer pole 84 is magnetized diametrically by the driving flux flow. Rotating vector 70 may be seen as a rotating bar permanent magnet i.e. the effective portion of the driving flux path instantaneously in time. The coupling coefficient is effectively reduced to two arcuate portions (ap0 and ap180) of the annular gap 96 in FIG. 14 (annular gap 96 is drawn oversized for illustration). Tests have shown, if there is even a small irregularity in the width of annular gap 96, the tangential motion of ap0 and ap180 will produce a rotating incremental permeability effect generating an off-null signal. This effect is much more pronounced when the driving core is excited by the precessing elliptical waveforms as disclosed in pending patent application Ser. No. 08/599,775.

The Internal Field Stator Driving Core

FIGS. 6–9 are illustrative of a further embodiment of this invention, (an internal field driving stator).

Driving stator core 155a in FIG. 6 has an outside driving diameter 140, an inside diameter 141 (also used as a mounting bore for a central pole 186 in FIG. 9). Stator 155a is formed of a high permeability magnetic material such as ferrite, powered iron or laminated steel. For illustration simplicity, driving stator 155a is orthogonally divided into only four wound poles i.e. 158a–158b on the x-axis and 162a–162b on the y-axis. Winding slots 139a permit conventional winding insertion. FIG. 7, is a radial view of stator 155a showing a basic sine-cosine x-y winding structure 158a–158b, 162a–162b wound through slots 139a to form an external radiating rotating magnetic field.

FIG. 8, is an isometric view of assembled probe PSb with the driven element (cylindrical outer pole 184) mounted around driving stator 155a. Pick-up coil 190 is shown wound around cylindrical pole 186. The coplanar driving principle is symbolized by the S-N dipole action of rotating vector 70 across the annular sensing face 179. Other conventional poly-phase pole combinations (odd or even) are deemed covered by this disclosure.

A greater number of pole segments provide more perfect circularity to the rotating driving field 70. Well known motor stator sinusoidal winding patterns are utilized for optimum poly-phase distributions. The integrated pick-up elements of polar coordinates sensor PSb are disposed both inside and outside the driving core 155a (FIGS. 8 and 9.), comprising a central cylindrical pole 186 and a cylindrical outer pole 184, both being formed of a high permeability low conductivity material/materials such as ferrite. FIG. 9 is a cross-sectional view taken along lines CC. The expanding internal driving flux is coupled from driving core 155a to the lower longitudinal portion of the cylindrical outer pole 184, and thence to the fringing sensing pattern. An axial portion of central cylindrical pole 186 is concentrically positioned within bore 141 (also called the I.D. of driving core 155a). In this embodiment there are two annular locations for incorporating the mentioned coupling coefficient (synergism term II): (a) an annular gap between driving core 155a and the cylindrical outer pole 184. (b) an annular gap 141a between central pole 186 and driving core 155a. Around central pole 186 is wound pick-up coil 190a. A nonferrous washer 199 encircles central pole 186 between the excitation windings and the pick-up coil windings as a high reluctance barrier to stray flux leakage from the excitation coils 158a, 158b, 162a, 162b. Washer 199 may be alternately utilized as a shorted pick-up coil turn or formed as multiple turns of thin flat stock wound in a tight longitudinal spiral (insulation between adjacent turns). The shorted turn version has a Lenz reflective flux interaction with the afore described coplanar disposed driving flux in the plane of the pick-up coil.

Surplus driving flux generated in the rear of driving core 155b may be repelled toward the sensing face for greater efficiency by means of a copper repulsion ring 167, as seen in FIGS. 8, 9. Repulsion ring 167 is isometrically illustrated in FIG. 9A, comprising an outer diameter 168, an inner diameter 169 and a longitudinal length 181. Excitation and pick-up coil connecting leads are not shown in any drawing figures for clarity.

External-Internal Field Stator Driving Core

FIG. 9, also illustrates an internal-external field driving combination PSx, by addition of stator 155b concentrically around a cylindrical outer pole 184, having a conducting thickness 184a. Stator 155b has excitation windings 158c. Although mechanically obvious, the vectorial sum of dual excitation possibilities are not readily apparent. The resultant excitation of cylindrical outer pole 184 by driving cores 155a and 155b may have the same frequency and in phase for greater driving flux, or e.g. different frequencies (two excitation sources) for harmonic generation (odd/even) in the resultant sensing pattern. The two driving fields may even counter-revolve at same/different angular velocities to provide a steerable beacon-like sensing pattern as disclosed in patent application Ser. No. 08/685,854. A disadvantage of the driving core embodiments of FIGS. 1–9 is the longitudinal winding slots 39a, 139a which are widened areas in the coupling coefficient gap between the driving and pick-up core. FIGS. 8, 9, also show a non-ferrous repulsion ring 167 around the rear portion of driving core 155a for driving field enhancement. This enhancement means serves a dual purpose: (1) repelling the driving flux toward the sensing end, (2) the I.D. of ring 167 may be made slightly larger than the O.D. of core 155a, as a flux concentricity adjustment means to compensate for manufacturing flaws. FIG. 10 is an isometric view (including a cut-away section) of probe PSc, which embodies elements of probes PSa, PSb, plus further utilization of high and low reluctance elements to enhance the resultant sensing pattern.

Figure 11:
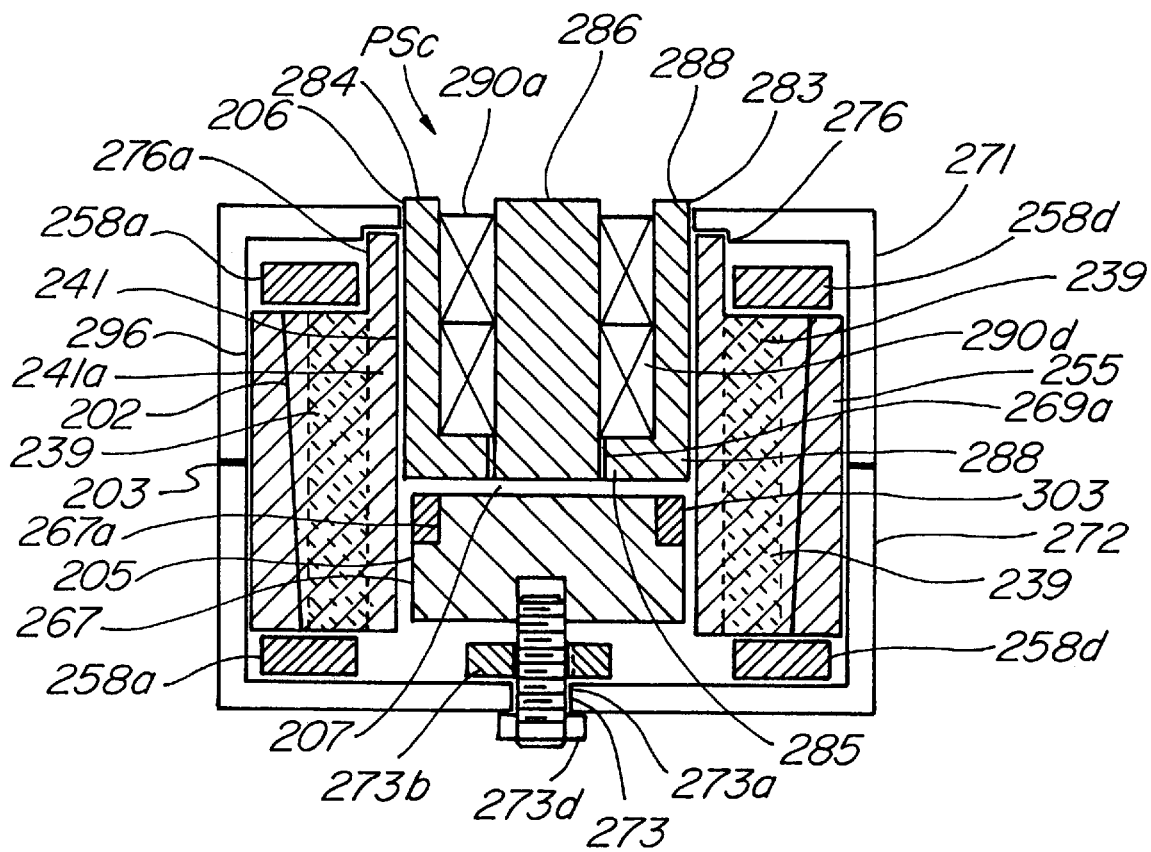
FIG. 11, is a cross-sectional view of probe PSc of FIG. 10.
Figure 12:
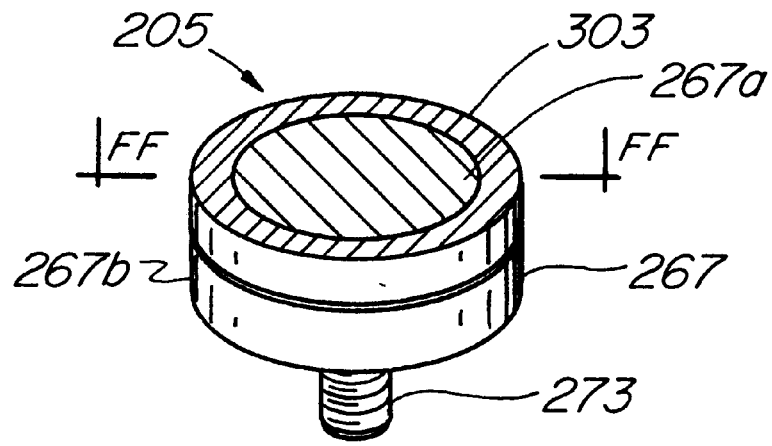
FIG. 12, is an isometric view of a flux symmetry slug 205 for probe PSc.
Figure 13:
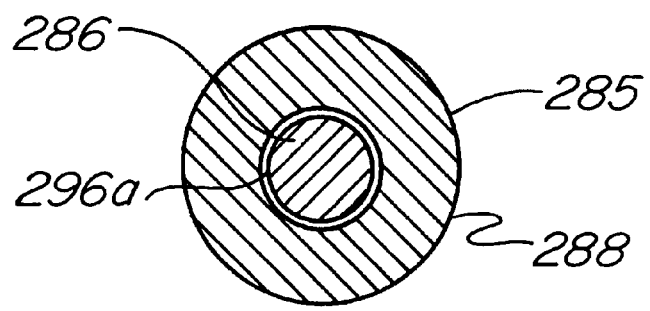
FIG. 13, is a base portion view of a polar sensor pick-up core having an integral annular magnetic gap 296a for determining coefficient of coupling as also shown cross-sectional in FIG. 11.

A nonferrous (copper) sensing end cap 271 is a dual utilization of the previously disclosed non-ferrous washer magnetic shield idea. The primary purpose of sensing end cap 271 is to concentrically support the outer pole 84, 184, 284 (pick-up core element) partially within the driving core 55a, 155b, 255a. The second purpose of copper sensing end cap 271 is to block away from the sensing pattern any stray flux leaking from the driving core 255a and the excitation windings. The disadvantage of the winding slot 39a, 139a openings breaking into the coupling coefficient gap (96a in FIG. 3) is eliminated in FIGS. 10, 11, by locating winding bores 239 away from the mounting bore 241 (stator I.D.) forming an integrate portion 241a. Longitudinally adjoining integrate portion 241a is coupling flange 276 for utilization of excitation winding 258a, 258b, 258c, 258d, clearance space at the top in FIG. 11. Annular space 279 is provided for pick-up coils 290a, 290b. Driving stator core 255 may be made separable for winding facility by a cone separation means 202, a cone being the least flux leakage separation means. FIG. 11 is a cross-section longitudinal view taken along lines FF in FIG. 10 of probe PSc, showing the concentric construction of flux concentricity slug 205. Slug 205 is further shown isometrically in FIG. 11, comprising a ferromagnetic portion 267 having a greater diameter 267b and a lesser diameter 267a. Concentrically fitted around lesser diameter 267a is a copper ring 303 producing an annular high reluctance area at the base portion 285 of pick-up core 288. Slug 303 is adjustably mounted to rear end cap 272 by means of slug screw 273, and made eccentrically adjustable by nuts 273b, 273d. Sensing end cap 271 and rear end cap 272 are joined around driving core 255 at 203 forming a casing. This nonferrous casing form may also be used with probes PSa, PSb, PSx. FIG. 13 illustrates an alternate coupling coefficient annular gap 296a within the base 285 of pick-up core 288 i.e central pole 286 is coupled to the base portion 285 by a coefficient. There are two pick-up coils 290a, 290b, wound around a central cylindrical pole 286 in a longitudinal arrangement.

I claim:
1. An eddy current probe comprising:
  a) a cylindrical outer pole formed of a high permeability magnetic material, said cylindrical outer pole being longitudinally divided into a driving length and a sensing length;
  b) a cylindrical central pole formed of a high permeability magnetic material, said cylindrical central pole being divided into a first axial length and a second axial length, the first and second axial lengths being approximately equal;
  c) an external radiating driving stator formed of a high permeability magnetic material, the said driving stator further comprising:
    i) a hollow cylinder having an outside diameter and a bore formed, around a common axis, and;
    ii) a plurality of longitudinal winding slots formed into the outer diameter leaving an equal plurality of pole segments extending radially outward from the central axis, and;
    iii) a plurality of poly-phase excitation coils wound within the longitudinal winding slots in a sinusoidal distribution, said excitation coils having connection leads, and;
    iv) poly-phase excitation being applied to the said excitation coils for inducing a rotating magnetic field within the said driving stator;
  d) the said driving stator being coaxially mounted within the driving portion of the cylindrical outer pole for coupling the rotating magnetic field to the said sensing portion;
  e) the said cylindrical central pole being coaxially mounted within the said bore a distance equal to the first axial length, and;
    i) the second axial length of the cylindrical central pole extending coaxially the sensing length of the cylindrical outer pole, further comprising an annular sensing face;
  f) a pick-up coil of many turns wound around the cylindrical central pole for generating a polar coordinates signal;
    i) said pick-up coil having connecting leads.
2. An eddy current probe comprising:
  a) a cylindrical outer pole formed of a high permeability magnetic material, said cylindrical outer pole being longitudinally divided into a driving length and a sensing length;
  b) a cylindrical central pole formed of a high permeability magnetic material, said cylindrical central pole being divided into a first axial length and a second axial length, the first and second axial lengths being approximately equal;
  c) an external radiating driving stator formed of a high permeability magnetic material, the said external radiating driving stator further comprising:
    i) a hollow cylinder having an outside diameter and a bore formed, around a common axis, and;
    ii) a first plurality of longitudinal winding slots formed into the outer diameter leaving an equal plurality of pole segments extending radially outward from the central axis, and;
    iii) a first plurality of poly-phase excitation coils wound within the longitudinal winding slots in sinusoidal distributions, each coil having connection leads, and;
    iv) a first source of poly-phase excitation being applied to the said first plurality of poly-phase excitation coils for inducing a rotating magnetic field within the said external radiating driving stator;
  d) the said external radiating driving stator being coaxially mounted within the driving portion of the cylindrical outer pole for coupling a first rotating magnetic field to the said sensing portion;
  e) the said cylindrical central pole being coaxially mounted within the said bore a distance equal to the first axial length, and;
    i) the second axial length of the cylindrical central pole extending coaxially the sensing length of the cylindrical outer pole to further comprise an annular sensing face;
  f) a pick-up coil of many turns wound around the cylindrical central pole for generating a polar coordinates signal;
    i) the said pick-up coil having connecting leads;
    ii) the said many turns being coplanar to the first rotating magnetic field for signal nulling, and;

g) an internal radiating driving stator formed of a high permeability magnetic material, the said internal radiating driving stator further comprising:
  i) a hollow cylinder having an outside diameter and an inside diameter formed around a common axis;
  ii) a second plurality of longitudinal winding slots formed into the said inside diameter leaving an equal plurality of pole segments extending radially inward toward the common axis, and;
  iii) a second plurality of poly-phase excitation coils wound within the second plurality of longitudinal winding slots in sinusoidal distributions, and having connection leads;
  iv) a second source of poly-phase excitation being applied to the second plurality of poly-phase excitation coils for inducing a rotating magnetic field within the said internal radiating driving stator;
h) the said internal radiating driving stator being coaxially mounted around the cylindrical outer pole, further being longitudinally disposed within the said driving portion for coupling a second rotating magnetic field to the said sensing portion of the cylindrical outer pole for combining two driving fields at the said annular sensing face.

3. The eddy current probe as defined in claim 2, wherein the said first and second sources of poly-phase excitation have the same frequency and phasing for a resultant additive driving flux vector.

4. The eddy current probe as defined in claim 2, wherein the said first source of poly-phase excitation frequency is a sub-multiple of the said second poly-phase excitation frequency.

5. The eddy current probe as defined in claim 2, wherein the said first and second sources of poly-phase excitation have predetermined variable frequencies and phasing for a steerable resultant flux vector fringing from the said annular sensing face.

* * * * *